(12) United States Patent
Wakil et al.

(10) Patent No.: US 9,271,647 B2
(45) Date of Patent: Mar. 1, 2016

(54) METHODS FOR OBJECTIVELY DETERMINING THE VISUAL AXIS OF THE EYE AND MEASURING ITS REFRACTION

(71) Applicants: Joe S. Wakil, Houston, TX (US); Paul van Saarloos, Balcatta (AU); Vasyl Molebny, Kiev (UA); Sergiy Molebny, Kiev (UA)

(72) Inventors: Joe S. Wakil, Houston, TX (US); Paul van Saarloos, Balcatta (AU); Vasyl Molebny, Kiev (UA); Sergiy Molebny, Kiev (UA)

( * ) Notice: Subject to any disclaimer, the term of this patent is extended or adjusted under 35 U.S.C. 154(b) by 0 days.

(21) Appl. No.: 14/102,257

(22) Filed: Dec. 10, 2013

(65) Prior Publication Data

US 2014/0160438 A1 Jun. 12, 2014

Related U.S. Application Data

(60) Provisional application No. 61/735,412, filed on Dec. 10, 2012.

(51) Int. Cl.
*A61B 3/14* (2006.01)
*A61B 3/00* (2006.01)
*A61B 3/107* (2006.01)
*A61B 3/10* (2006.01)
*A61B 3/103* (2006.01)

(52) U.S. Cl.
CPC .............. *A61B 3/107* (2013.01); *A61B 3/1015* (2013.01); *A61B 3/0025* (2013.01); *A61B 3/103* (2013.01)

(58) Field of Classification Search
CPC .............................. A61B 3/1015; A61B 3/152
USPC .................................................. 351/208, 246
See application file for complete search history.

(56) References Cited

U.S. PATENT DOCUMENTS 6,217,570 B1 4/2001 Nevyas
2010/0271595 A1* 10/2010 Molebny ........................ 351/221

OTHER PUBLICATIONS

Nevyas operative ketometer/fixation system instructions for use, Varitronics, Inc., 2004, [online] Retrieved from the Internet: <URL: http://www.varitronics.com/pdf/360user.pdf>; entire document.
Bradley, A et al. Modeling off-axis vision-1: the Optical effects of decentering visual targets or the eye's entrance pupil. 1995. [online] Retrieved from the Internet: <URL: http://research.opt.indiana.edu/Library/ModelOffAxisl/ModelOffAxisl.html>; entire document.

* cited by examiner

*Primary Examiner* — Mahidere Sahle
(74) *Attorney, Agent, or Firm* — Benjamin Aaron Adler (57) ABSTRACT

Provided are methods for determining an axis of best vision of an eye or for objectively determining a visual axis of an eye and for making the most accurate measurement of refraction. Generally, an optical measuring device or instrument projects laser beams into the eye during a scan. Positions of the projected beams are detected and measured on the retina to produce a set of projections. Wave front tilt of radiation that is backscattered from the retina is calculated as a best fit from the set of projections. The axis of best vision or the visual axis is reconstructed from a set of those traces of chief rays exiting from the eye that cross the nodal point of the optical system of the eye and that are normal to the wave front tilts. Measuring with the Styles Crawford scans centered over this axis provides the most accurate objective refraction.

8 Claims, 10 Drawing Sheets

METHODS FOR OBJECTIVELY DETERMINING THE VISUAL AXIS OF THE EYE AND MEASURING ITS REFRACTION

CROSS-REFERENCE TO RELATED APPLICATIONS

This application is a nonprovisional under 35 U.S.C. §119 (e) of provisional application U.S. Ser. No. 61/735,412, filed Dec. 10, 2012, now abandoned, the entirety of which is hereby incorporated by reference.

BACKGROUND OF THE INVENTION

1. Field of the Invention

The present invention relates generally to the fields of ophthalmic instruments that are used to examine the eye. More specifically, the present invention relates to ophthalmic examination instruments that measure and characterize the properties of the eye with high accuracy of their localization.

2. Description of the Related Art

The eye is not an ideal optical system and, therefore, different reference axes can be used to describe its properties in a 3D space. These properties cannot be comparable unless they are calculated with respect to the same reference axis. Four axes are used: optical axis, pupillary axis, line of sight, and visual axis. Similarly to the perfect optical systems, the optical axis of the eye crosses the optical centers of two main optical components, the cornea and the crystalline lens.

In the first steps of aberrometry development, the sub-commission of the Optical Society of America (OSA) working group recommended to the ophthalmic community to use the line of sight as the reference axis for the purposes of calculating and measuring the ocular optical aberrations (1). One of the arguments was that the center of the pupil can be easily designated. In parallel, the visual axis was often taken for the reference, especially in corneal topography, because it was easily identified using Purkinje reflections from the anterior cornea. Having different reference axes in corneal topography, in optical coherence tomography, in aberrometry, in refractometry, etc., caused difficulties when trying to integrate the data from separate instruments. The surgeons discovered worse vision correction in patients with higher angle kappa, i.e., higher angular distance between the pupillary axis and visual axis.

The cause of such statistics was the usage of an incorrect reference axis when performing the surgery. Usually, the eye is pupillary centered during the surgery, meanwhile, the imaging in the eye is taking place through the nodal point which is the case when measuring the aberrations. The major reason for this is the current misconception among many laser companies and surgeons that ablations are centered on the entrance pupil centre instead of the visual axis. In eyes with a large angle kappa, centering the ablation on the entrance pupil centre will result in the creation of a new vertex, whereas the natural vertex is maintained if the ablation is centered on the corneal vertex (2).

In the US Patent Publication 20100114076, a method of performing refractive laser eye surgery on a human eye is disclosed where the ablation pattern is centered along the visual axis, rather than along the line of sight. A wavefront, either ocular, corneal or a combination thereof, is generated by a wavefront sensor centered along the line of sight. Then, an analysis pupil is determined that is centered along the visual axis at the point of intersection with the cornea. The reconstruction of the measured wavefront is done through a least squares fit of a series of slopes from the measured wavefront and/or through the transformation of aberration coefficients. Finally, an ablation pattern, or a lenticule generation pattern, to be performed by a refractive laser centered on the corneal intersect of the visual axis, is produced in accordance with the reconstructed wavefront. However, there is no disclosure on how a new, analysis pupil is determined nor how the point of corneal intersection is found.

In practice, the visual axis is determined subjectively. The patient is asked to orient his sight to overlay two targets, near and far, positioned on the optical axis of the measuring instrument. With this orientation of the eye, measurement of eye parameters is made, for example, with a ray tracing aberrometer (3). Simultaneously, an image of the pupil is registered. On this image, the position of the optical axis of the measuring instrument is identified as the center of the set of measuring laser beams. This position is taken also for reference to identify the visual axis of the eye.

A drawback of this approach is in the uncertainty of its subjective procedure. The accuracy depends on a subjective patient's estimate, not on objective measurement. Subjective judgement is difficult because it is impossible for both points to be in focus for the patient. However, objective measurements allow one to determine the point of the corneal intersection by the visual axis, and to take into account a corresponding shift of eye parameters respectively the pupil, and to use these data to measure any other characteristics of the eye, or to correct the refraction map for vision correction by means, for example, of the corneal tissue ablation.

Thus, there is a recognized need in the art for improved methods for determining the trace of the visual axis objectively without depending on a patient's estimates. Particularly, the prior art is deficient in methods for objectively determining the axis of best vision of the eye. The present invention fulfills this longstanding need and desire in the art.

SUMMARY OF THE INVENTION

The present invention is directed to a method for determining an axis of best vision of an eye. The method comprises scanning a wavefront measurement device around a plurality of axes in the eye to project laser beams therein. The positions of the projected beams are detected and measured on the eye's retina to produce a set of projections. A best fit curve is calculated from the set of projections to determine an axis with a minimum of aberrations which comprises the axis of best vision of the eye.

The present invention also is directed to method for objectively determining a visual axis of an eye. The method comprises aligning an optical axis of a measuring instrument with an unambiguously determinable axis of the eye, said aligning determining the visual axis of the eye.

The present invention is directed to a related method for objectively determining a visual axis of the eye. The method comprises projecting a set of narrow laser beams into the eye and detecting and measuring positions of the projections on the retina. A wave front tilt of radiation backscattered from the retina is calculated as a best fit from the set of projections. The visual axis is reconstructed from a set of traces of chief rays exiting from the eye that cross the nodal point of the optical system of the eye and that are normal to the wave front tilts.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, "papillary axis" refers to the perpendicular to the anterior corneal surface and crosses the center of the pupil.

As used herein, "line of sight" refers to the connection between the point target, to which the eye is oriented, and the center of the pupil.

As used herein, "visual axis" refers to an axis that also is directed on the point target crossing it, but inside the eye. The visual axis crosses the first nodal point, not the center of the pupil.

As used herein, "Purkinje image of the eye" refers to a virtual reflection of the coaxial light fixation source off of the cornea's surface as the eye under measurement is properly fixating.

As used herein, "true visual axis" refers to the line from the optical nodal point of the eye to the point of regard, whereby the nodal point of the eye is determined by knowing the exact location and optical characteristics of all elements of the eye and their relationship to each other.

In one embodiment of the present invention there is provided a method for determining an axis of best vision of an eye, comprising scanning a wavefront measurement device around a plurality of axes in the eye to project laser beams therein; detecting and measuring positions of the projected beams on the eye's retina to produce a set of projections; and calculating a best fit curve from the set of projections to determine an axis with a minimum of aberrations, said axis comprising the axis of best vision of the eye.

In this embodiment the calculating step may comprise weighting slopes of the projections by a factor substantially similar to a Styles Crawford effect except that a distance from the axis instead of from a pupil of the eye is used. Also in this embodiment the best fit curve may comprise the wave front tilt of the radiation backscattered from the retina. In addition the axis of best vision may be a true visual axis of the eye.

In another embodiment of the present invention there is provided a method for objectively determining a visual axis of an eye, comprising aligning an optical axis of a measuring instrument with an unambiguously determinable axis of the eye, said aligning determining the visual axis of the eye.

In this embodiment the aligning step may comprise projecting a set of narrow laser beams into the eye; detecting and measuring positions of the projections on a retina of the eye; calculating a wave front tilt of radiation backscattered from the retina as a best fit from the set of projections, and reconstructing the visual axis from a set of traces of chief rays exiting from the eye crossing the nodal point of the optical system of the eye that are normal to the wave front tilts.

In an aspect of this embodiment the set of projections is provided in a central zone of a pupil of the eye or may be scanned over any zone in the pupil and the crossings of the anterior surface of the cornea by the laser beams encircle the unambiguously determinable axis of the eye where the calculating step may comprise averaging the tilts of all separate laser beams. Further to this aspect, the method may comprise scanning additional sets of projections to search for a best determination of the visual axis.

In another aspect the set of projections is provided in the central zone of the pupil and the crossings of the anterior surface of the cornea by the laser beams encircle the unambiguously determinable axis of the eye where the calculating step may comprise applying a Zernike decomposition to determine tilt components thereof.

In this embodiment and all aspects thereof the unambiguously determinable axis of the eye may be the axis crossing the vertex of an anterior surface of a cornea and is perpendicular to the vertex where perpendicularity of the unambiguously determinable axis is checked by a first Purkinje reflection. Also, the unambiguously determinable axis of the eye is an axis with a lowest number of aberrations. In addition a density of each of the projected laser beams may be adjusted to provide weighting to match a Styles Crawford effect.

Also in this embodiment and all aspects the set of projections may be provided with tilts in a range of values of an angle kappa. In an aspect thereof the best fit of the angle kappa may be determined as having a minimal difference between the tilt of the projected beam and the tilt of the chief ray exiting from the eye. Alternatively, the set of projections may be provided with tilts from 0 degrees to about 10 degrees from the pupillary axis.

Determining the refraction of the human eye has been a goal for diagnostic optical systems, since the inception of the auto-refractor. Common refraction today is provided in Sphere, Cylinder and Axis terms which enable spherocylindrical correction such as with glasses and contact lenses so that light is optimally focused on the retina in an eye that is not emmetropic. Eyes that are myopic, hyperopic, presbyopic and/or astigmatic are classic examples of eyes that need optical correction to see normally as currently described with 20/20 vision by the traditional Snellen Acuity chart for example.

A method of measuring the eye with scanning beams of light that can be done sequentially or simultaneously in a sampling method of measuring forward aberrations of light can help determine the real visual axis of the eye by using an external diagnostic device. By knowing where the true visual axis of the eye is and its location on the cornea as shown within or outside the entrance pupil of the eye provides for a critical new parameter that can now be used to dramatically improve the accuracy of objective determination of refractive errors of eyes both human and otherwise and therefore to correct such refractive errors whether just simply spherocylindrical and or higher order aberrations through custom or individualized refractive corrective procedures as desired.

By knowing the exact location of the true visual axis within the entrance pupil, an improved measure of refraction of the eye can be made, i.e., one that is centered over this true visual axis. As is currently standard in the art, the first Purkinje image of the eye is used as the best estimate for the true visual axis of the eye. This point together with center of the entrance pupil or line of sight are commonly used to center the measurement of the refractive error of the eye. Automatic and manual devices which utilize streak retinoscopy, Hartmann Shack aberrometry, Talbot Moire, Tscherning aberrometry and/or using Ray Tracing amongst other forms of refraction/aberrometry measurement principles have traditionally used the line of sight, or center of the entrance pupil or exit pupil as the center of measurement and/or use the first Purkinje image that is an estimate of visual axis of the eye. These points of centration also are used routinely to determine the higher order aberrations of the eye with wavefront devices or devices that do ray tracing and similar measurements.

The scanning schema provided herein can be performed in a myriad of patterns and sizes all of which have the goal of determining the ultimate true visual axis of the eye as being a reciprocal direction of the eye's visual axis. In determining such axis a measurement is then made over the entire entrance pupil or any part thereof as desired using the location of the true visual axis at the optical center of measurement and as such derive the refractive correction of the eye using either lower order aberrations such as Sphere, Cylinder or Axis with or without higher order aberrations such as Coma, Spherical Aberration and Trefoil. Such diagnostic measurement can provide optimal refractive correction for the eye in an objective and automated fashion that could make subjective and manual techniques obsolete given the instabilities and subjective nature of manifest refraction.

With the means to determine the true visual axis as described herein, the ability to diagnose ocular vision and to treat or improve such vision can be advanced. Procedures to correct vision via spectacles and contact lenses or via surgical intervention, as with refractive lasers, IOL implant (cataract surgery), corneal inlay implantation, intra-ocular contact lenses or any other means within the eye or on the ocular surface, can be enhanced with such information as to where the location of the true visual axis is manifested and identified. Knowing where best to have optical centration of vision corrective procedures whether using additive approaches or modifying existing structures of the eye is necessary to optimize outcomes and provide desired visual outcome.

The success of vision correction using the corneal tissue ablation, customized contact lenses or intraocular lenses depends, among other factors, on the adequate selection of the coordinate system for describing the refraction errors when measuring the aberrations and when correcting them. It is a normal practice to use 2D imaging of the eye in the process of surgery. It is important to have in this 2D image the reference coordinates where the visual axis crosses the anterior surface of the cornea.

Provided herein are methods of objectively determining the axis of the eye with the optical axis of a measuring instrument aligned with an unambiguously determinable axis of the eye. Generally, alignment is based on projecting a set of narrow laser beams into the eye and detecting and measuring positions of their projections on the retina. The unambiguously determinable axis of the eye is the axis which crosses the vertex of the anterior surface of the cornea and is perpendicular to the vertex. Perpendicularity may be checked by the first Purkinje reflection. The wave front tilt of the radiation backscattered from the retina may be calculated as the best fit from the set of projections. The axis is reconstructed from the set of traces of the chief rays that cross the nodal point of the optical system of the eye that are normals to the wave front tilts.

The set of projections may be provided in the central zone of the pupil. The crossings of the anterior surface of the cornea by the laser beams encircle the unambiguously determinable axis. Calculation of the best fit of the wave front tilt of the radiation backscattered from the retina is provided by averaging the tilts of all separate laser beams. Alternatively, calculation of the best fit of the wave front tilt of the radiation backscattered from the retina is provided as the tilt components of the Zernike decomposition.

Alternatively, the set of projections is provided in parallel to the optical axis of the measuring instrument. In another alternative method the set of projections have tilts in the range including the values of the kappa angle. As such, the best fit of the angle kappa is determined as having the minimal difference between the tilt of the projected beam and the tilt of the chief ray exiting from the eye. In yet another alternative method, the set of projections is not linked to the value of the kappa angle. The set of projections may have or a provide with tilts ranging from 0 degrees to about 10 degrees in regards to the pupillary axis. As such, the best fit of the visual axis is determined as having a minimal difference between the tilt of the projected beam and the tilt of the chief ray exiting from the eye.

Moreover, the methods provided herein measure the low order and the high order aberrations, so that the axis of optimal vision or the visual axis is determined by the axis that has the least high order aberrations. Utilizing scanning patterns with the Stiles Crawford effect has the benefit that the weighting of these measurements can be improved to be more physiologically correct. Also, the measurement now becomes a highly accurate objective refraction. Finding the best axis of vision, whether the axis is the most optimal axis or the true visual axis of the eye and then measuring with the Styles Crawford scans centered over this axis provides the most accurate objective refraction of the eye. In the methods provided herein, refraction can be presented just in terms of low order aberrations, i.e., Sphere and Cylinder, and optionally can include the higher order aberrations, for example, Coma, Spherical Aberration and Trefoil.

Particularly, methods are provide that utilize a lower density of points in the outer scan area and a higher density of points around the visual axis. The method simulates what the brain does, i.e., adjusting the eye to find the axis that gives the best image. To find the axis with the lowest aberrations, the weighting the eye gives to each ray entering the pupil must be mimicked. This is defined by the Styles Crawford effect, although not centered on the pupil as provided herein. Light hitting the retina at right angles is detected most efficiently.

The efficiency drops off at the cosine of the angle the ray hits the retina. By having a lower density of points in the outer scan, the lower contribution of this outer area to the calculation of aberrations can be utilized to match what happens to in the eye. During scanning peripherally to the edge of the pupil, the scan density drops off substantially so that these peripheral parts of the pupil have much less effect on the patients refraction and optical quality.

As described below, the invention provides a number of advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

Figure 1:
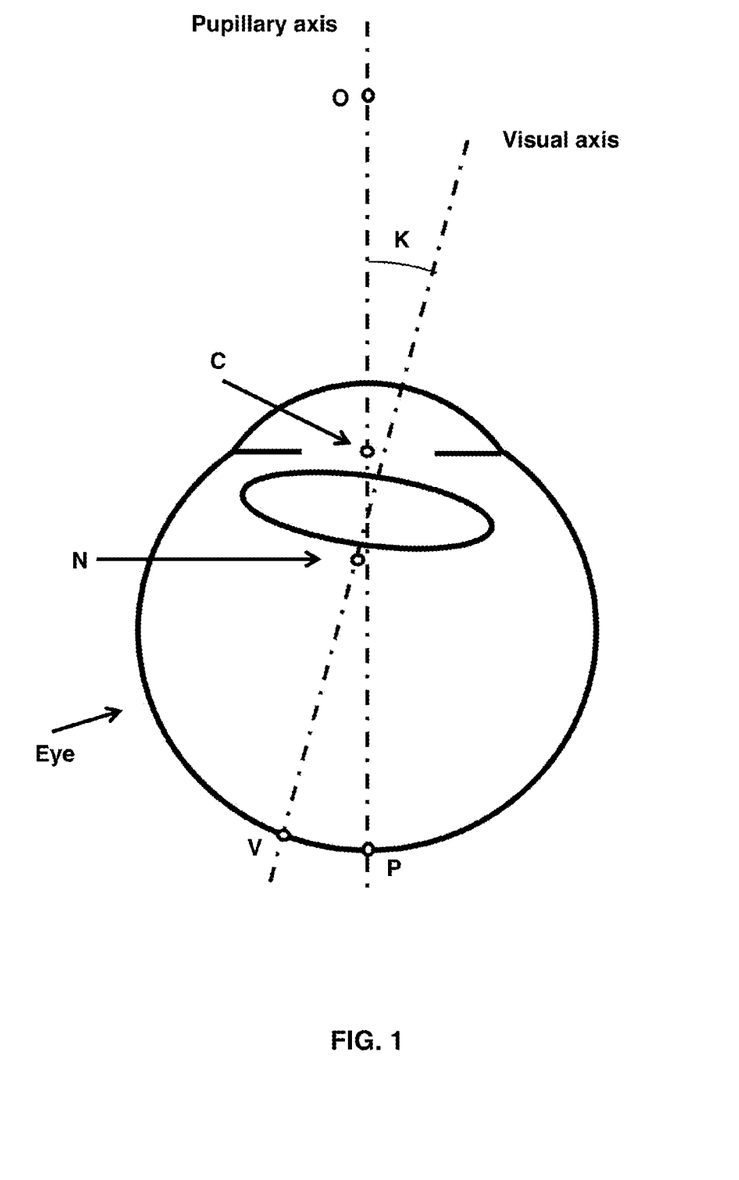
FIG. 1 illustrates the definitions of the pupillary and visual axes of the eye.

FIG. 1 is a diagram demonstrating the definitions of the pupillary and visual axes of the eye. In the eye the pupillary axis crosses the center of the pupil C and is oriented perpendicularly to the corneal apex. The visual axis crosses the nodal point N. The retina is crossed by the visual axis at point V, and by the pupillary axis at point P. The visual and pupillary axes are tilted in regards to each other at an angle κ (kappa).

Figure 2:
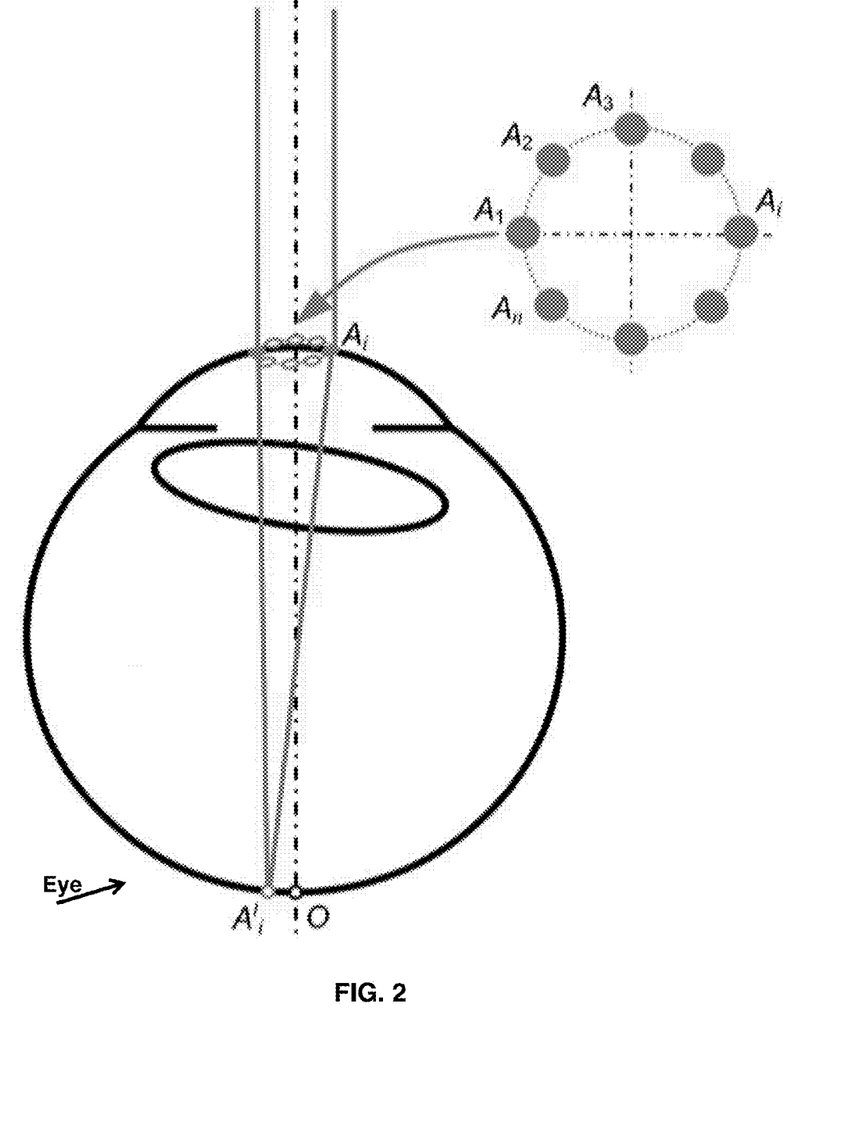
FIG. 2 depicts the projecting of a set of narrow laser beams in the eye in parallel to the optical axis of the measuring instrument.

FIG. 2 is a diagram illustrating a set of narrow laser beams projected in the eye. This set of beams encircles the pupillary axis and crosses the cornea in the points $A_1, A_2, A_3, \ldots A_i, \ldots A_n$, where n is enough to be no more than 10. If the eye is emmetropic, all of the beams cross the retina in the same point $A^1_i$. In case of ametropia, they are projected in a circle-like sequence of spots. These spots can be treated as the secondary sources of light that are imaged by an optical system looking into the eye. Their position in the focal plane of the optical system can be measured by a position sensing detector. From measured data, the tilt of the chief rays can be calculated and then averaged over the set of all laser beam projection.

Figure 3:
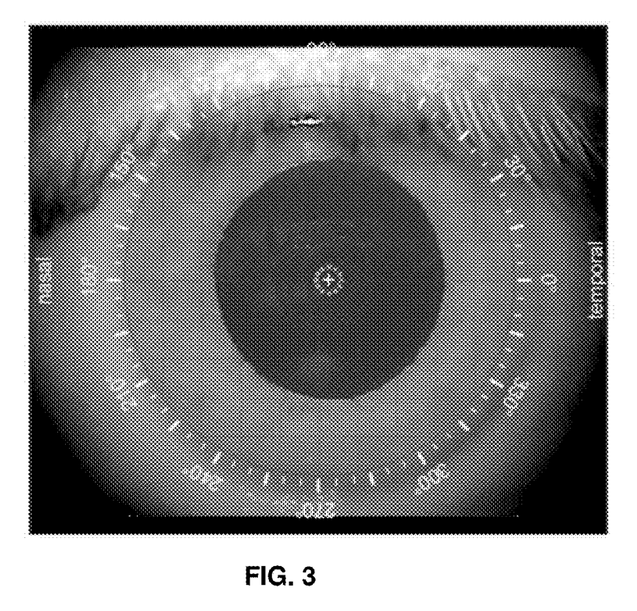
FIG. 3 depicts crossings of the anterior surface of the cornea by the set of laser beams encircling the central pupil zone.

FIG. 3 is an image of an eye with the points $A_1, A_2, A_3, \ldots A_i, \ldots A_n$, of the corneal crossings in the plane of the pupil displayed.

Figure 4:
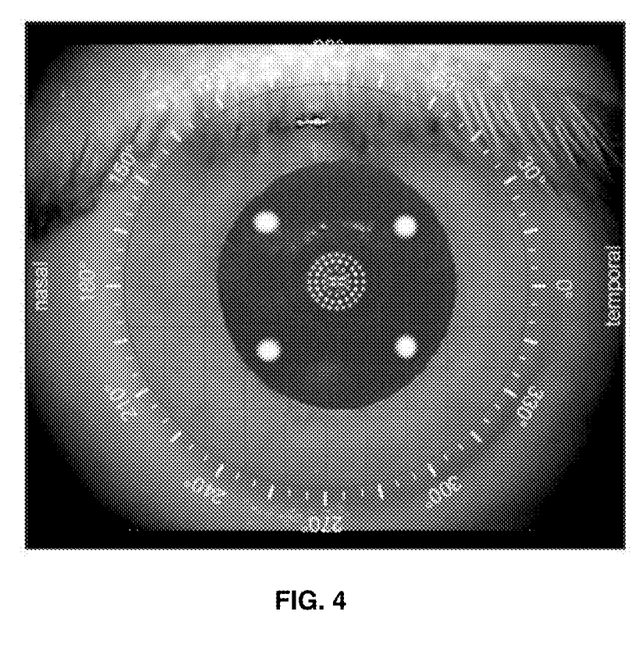
FIG. 4 depicts crossings of the anterior surface of the cornea by the set of laser beams filling the central pupil zone necessary to calculate the refraction map.

FIG. 4 illustrates an alternative approach to measuring the tilt of the wave front exiting from the eye. Similarly to the ray tracing aberrometry, the set of laser beams can fill-in the zone around the pupillary axis. Exiting radiation is used to measure the tilts of chief rays corresponding to each laser beam and to reconstruct the wave front in the small central zone having the smallest level of aberrations in comparison to larger zones of the pupil. After the best shape fit of the wave front using Zernike decomposition, one can get the averaged tilt of the exiting wave front from the tilt components of the Zernike decomposition.

Figure 5:
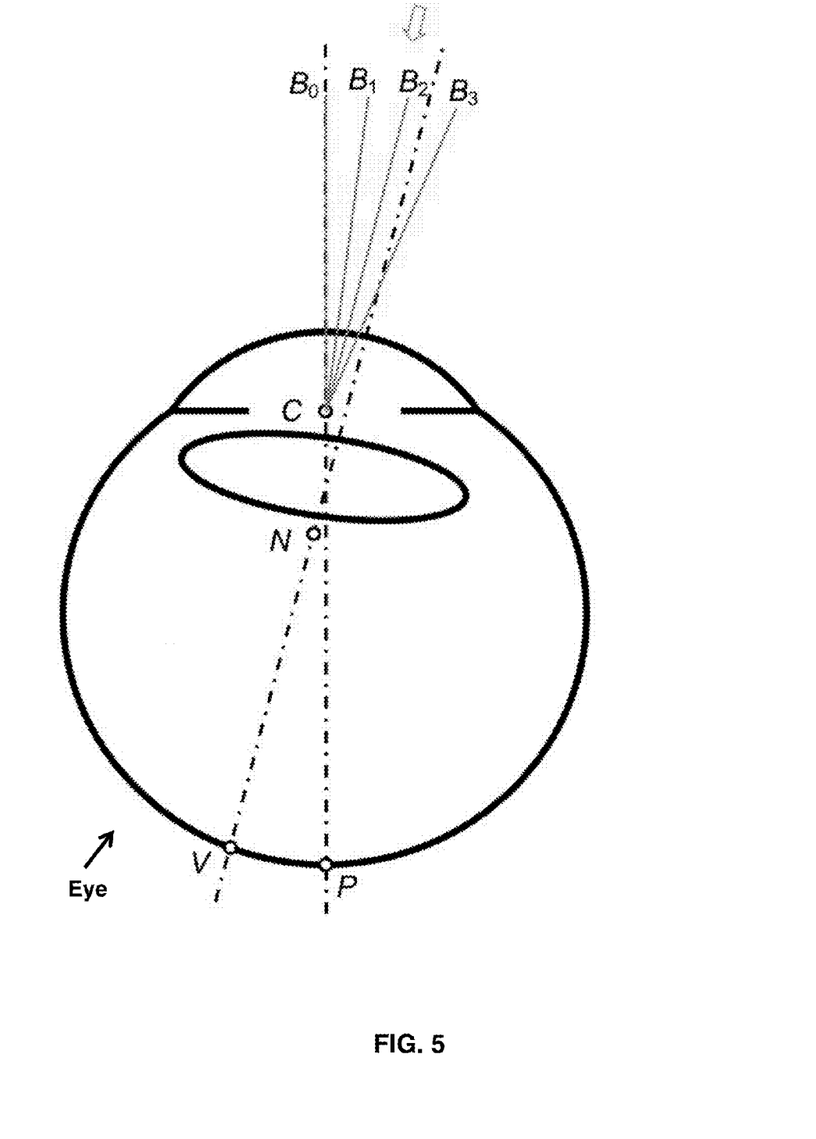
FIG. 5 depicts the projecting of a set of narrow laser beams in the eye crossing the center of the pupil at different angles.

FIG. 5 is a diagram illustrating that the best fit of the exiting wave front corresponding to the tilt of the visual axis can be achieved if using the set of laser beams projected in the eye at different angles.

Figure 6:
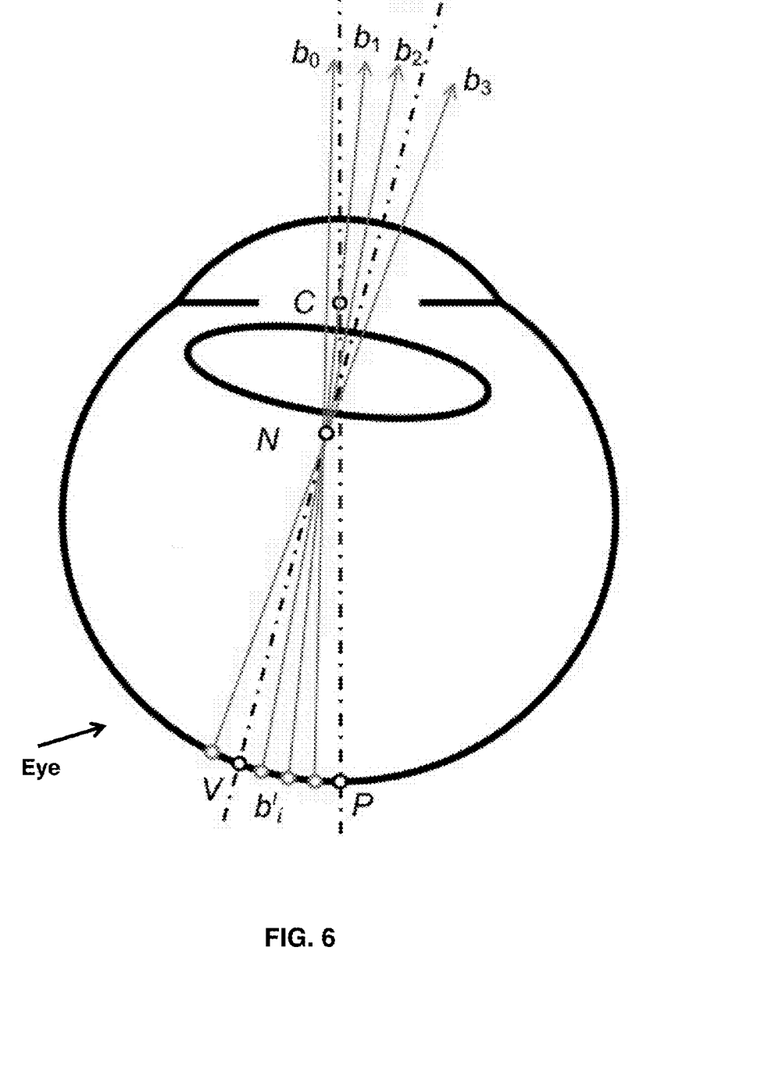
FIG. 6 depicts the chief rays of the radiation exiting from the eye emerging from the points of beam projections shown in FIG. 5.

FIG. 6 is a diagram illustrating the back traces of these projections. Among all the beams in FIGS. 5 and 6 there can be beams that have the projections on the retina where the visual axis crosses it. The chief backward ray from this point will follow the trace exactly coinciding with the visual axis. Comparing the tilts of the beams entering the eye with tilts of the chief rays of the radiation exiting from the eye, one can identify those that have the best fit and thus correspond to the visual axis of the eye.

Figure 7:
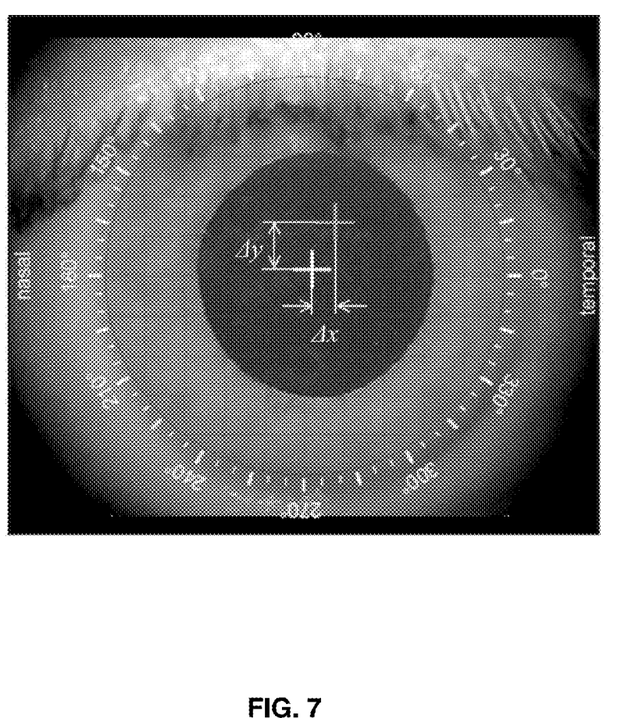
FIG. 7 illustrates positions of the cornea cross points with the pupillary and with the visual axis.
Figure 8A:
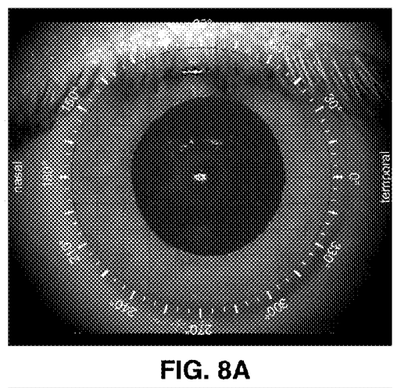
FIGS. 8A-8L depict scanning a very small region within the entrance pupil to locate the point of minimal aberrations (FIGS. 8A-8F) and show the corresponding retinal scans (FIGS. 8G-8L).
Figure 8B:
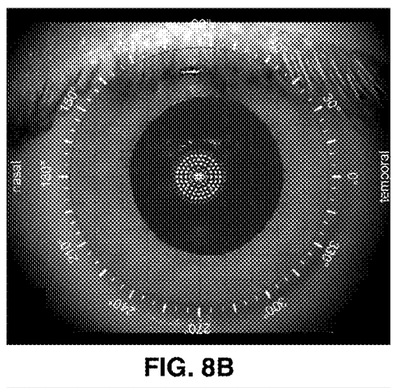
Figure 8C:
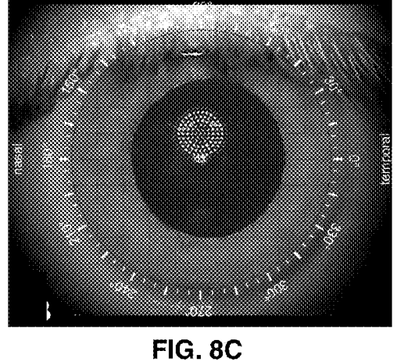
Figure 8D:
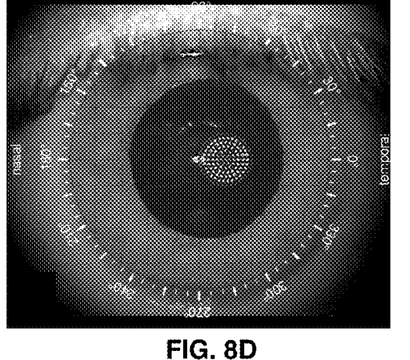
Figure 8E:
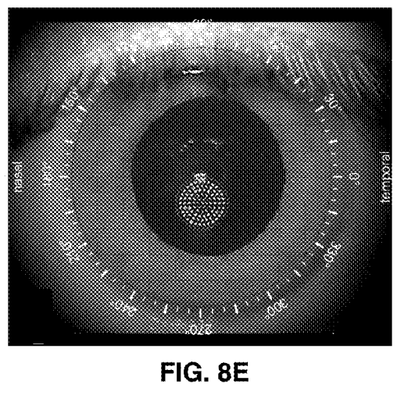
Figure 8F:
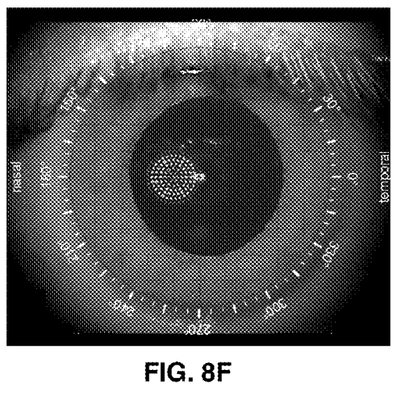
Figure 8G:
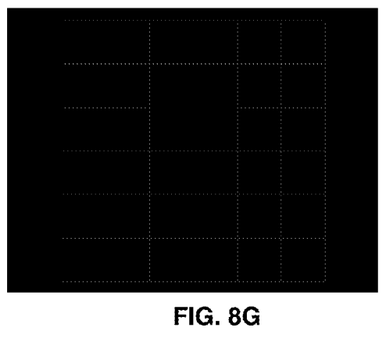
Figure 8H:
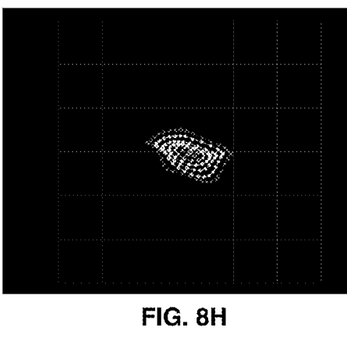
Figure 8I:
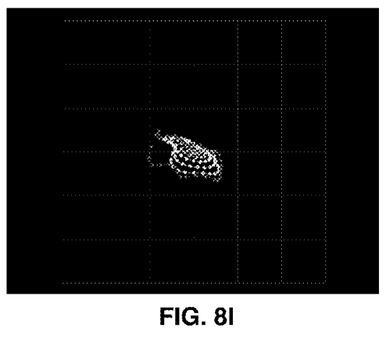
Figure 8J:
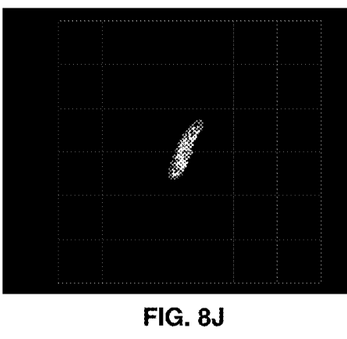
Figure 8K:
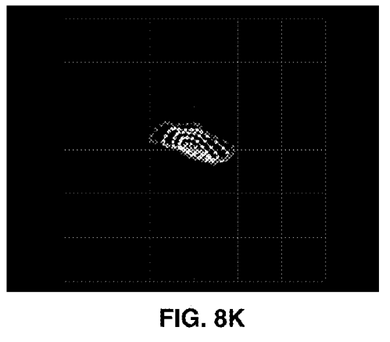
Figure 8L:
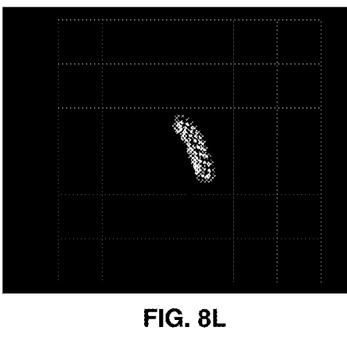

FIG. 7 is an image of the eye depicting the final result of the visual axis determination. Shown is the position of the point of the cornea crossing by the visual axis having the coordinates Δx and Δy in the plane of the pupil in regards to its center.

FIGS. 8A-8L are images of an eye illustrating means to determine the true visual axis of the eye and the retinal scans produced thereby. Such means may involve the use of thin beam optics such as ray tracing to determine the point of minimal aberrations within the eye that is consistent with the patient's fixation or point of gaze. For example, in FIGS. 8A-8F, a small concentric scan of rays of light that rapidly, either in sequence or simultaneously, are used to scan a very small region of the eye within the entrance pupil to locate the point of minimal aberrations. A first estimate would be to use the traditional first Purkinje image that is the widely used estimate of the visual axis of the eye. Using this point to make the first measurements to confirm whether the true visual axis is actually at this estimated location or another then the measurement process is repeated in a scanning pattern from the estimated location provided by the first Purkinje image to search for the true visual axis. FIGS. 8G-8L are the resultant retinal scans.

Figure 9:
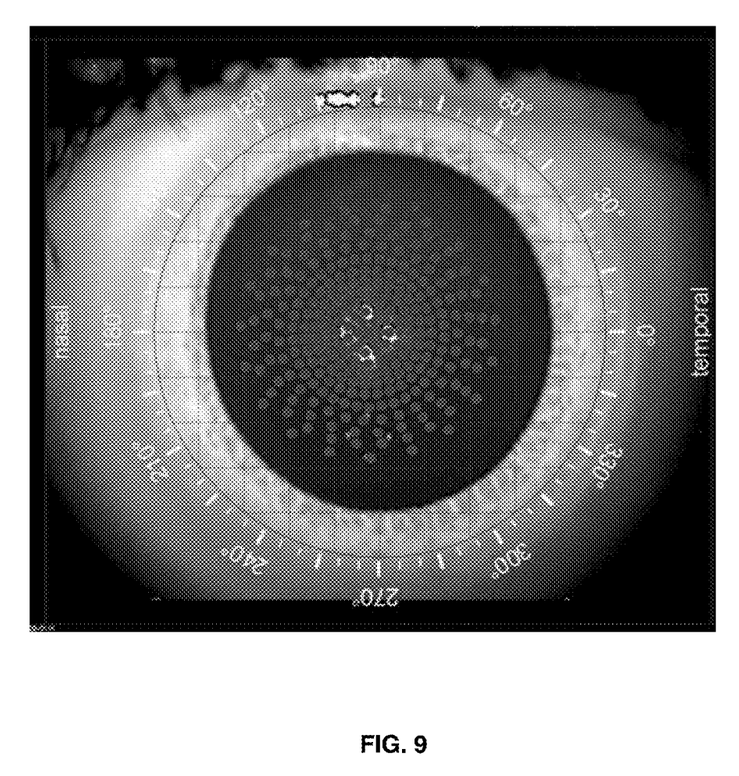
FIG. 9 depicts an SC scan pattern on an image of an eye.

FIG. 9 shows an SC scan pattern superimposed over an image of an eye. The pattern comprises 256 total points. The ring number and points per ring in the scan are shown in Table 1.

TABLE 1

| Ring | Scan Points |
|------|-------------|
| 1    | 1           |
| 2    | 6           |
| 3    | 11          |
| 4    | 16          |
| 5    | 22          |
| 6    | 27          |
| 7    | 31          |
| 8    | 37          |
| 9    | 31          |
| 10   | 27          |
| 11   | 28          |
| 12   | 29          |

Figure 10:
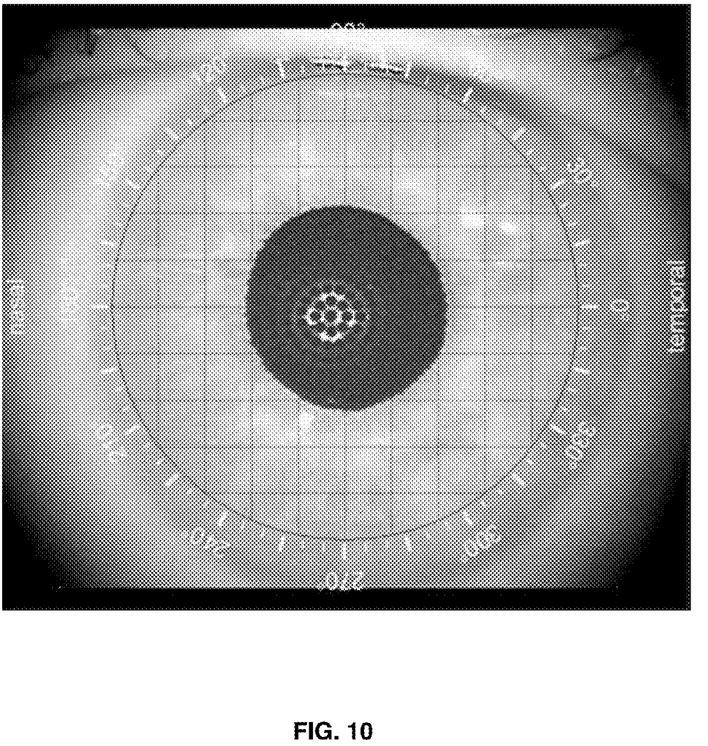
FIG. 10 depicts a scan pattern for an off-pupil center visual axis.

FIG. 10 shows a scan pattern adjusted for an off-pupil center visual axis superimposed over an image of an eye. The pattern comprises 128 total points. The ring number and points per ring in the scan are shown in Table 2.

TABLE 2

| Ring | Scan Points |
|------|-------------|
| 1    | 1           |
| 2    | 8           |
| 3    | 15          |
| 4    | 23          |
| 5    | 29          |
| 6    | 24          |
| 7    | 28          |

The following references are cited herein.
1. Applegate, et al. Journal of Refractive Surgery, 16:S655-S658, September/October 2000.
2. D. Reinstein. EuroTimes, p. 21, 9 Apr. 2012.
3. Tracey Technologies, Corp., Houston, Tex., see User Manual.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A method for objectively determining a visual axis of an eye, comprising:
    projecting a set of narrow, separate laser beams into a central zone of a pupil of the eye or into any zone in the pupil wherein crossings of an anterior surface of the cornea by said laser beams encircle an unambiguously determinable axis of the eye;
    detecting and measuring positions of the projections on a retina of the eye to provide a set of projections;
    averaging the tilts of all separate laser beams to calculate a wave front tilt of radiation backscattered from the retina as a best fit from the set of projections, and
    reconstructing the visual axis from a set of traces of chief rays exiting from the eye crossing the nodal point of the optical system of the eye that are normal to the wave front tilts.

2. The method of claim 1, further comprising:
    scanning additional sets of projections to search for a best determination of the visual axis.

3. The method of claim 1, wherein a density of each of the projected laser beams is adjusted to provide weighting to match a Styles Crawford effect.

4. The method of claim 1, wherein the set of projections is provided with tilts in a range of values of an angle kappa.

5. The method of claim 4, wherein the best fit of the angle kappa is determined as having a minimal difference between the tilt of the projected beam and the tilt of the chief ray exiting from the eye.

6. The method of claim 1, wherein the set of projections is provided with tilts from 0 degrees to about 10 degrees from the pupillary axis.

7. The method of claim 1, wherein the unambiguously determinable axis of the eye is the axis crossing the vertex of an anterior surface of a cornea and is perpendicular to said vertex, whereby perpendicularity of the unambiguously determinable axis is checked by a first Purkinje reflection.

8. The method of claim 1, wherein the unambiguously determinable axis of the eye is an axis with a lowest number of aberrations.

* * * * *